(12) United States Patent
Miyazaki et al.

(10) Patent No.: US 10,786,500 B2
(45) Date of Patent: Sep. 29, 2020

(54) STABLE PHARMACEUTICAL COMPOSITION FOR ORAL ADMINISTRATION

(71) Applicant: ASTELLAS PHARMA INC., Tokyo (JP)

(72) Inventors: Masakazu Miyazaki, Tokyo (JP); Ryohei Ishiba, Tokyo (JP); Yuki Takaishi, Tokyo (JP); Fumiaki Uejo, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

(21) Appl. No.: 15/741,377

(22) PCT Filed: Jul. 1, 2016

(86) PCT No.: PCT/JP2016/069615
§ 371 (c)(1),
(2) Date: Jan. 2, 2018

(87) PCT Pub. No.: WO2017/006855
PCT Pub. Date: Jan. 12, 2017

(65) Prior Publication Data
US 2018/0185359 A1    Jul. 5, 2018

(30) Foreign Application Priority Data
Jul. 3, 2015 (JP) ................ 2015-134817

(51) Int. Cl.
*A61K 31/497* (2006.01)
*A61K 47/26* (2006.01)
*A61K 47/10* (2017.01)
*A61K 9/20* (2006.01)

(52) U.S. Cl.
CPC ............ *A61K 31/497* (2013.01); *A61K 9/20* (2013.01); *A61K 9/2095* (2013.01); *A61K 47/10* (2013.01); *A61K 47/26* (2013.01)

(58) Field of Classification Search
CPC ......... A61K 31/497; A61K 9/20; A61K 47/10
USPC ..................................................... 514/252.1
See application file for complete search history.

(56) References Cited

U.S. PATENT DOCUMENTS

| | | | |
|---|---|---|---|
| 2012/0040968 A1 | 2/2012 | Shimada et al. | |
| 2013/0273161 A1 | 10/2013 | Bouillot et al. | |
| 2014/0371196 A1* | 12/2014 | Shimada | C07D 239/48 514/210.2 |
| 2016/0339020 A1 | 11/2016 | Eguchi et al. | |

FOREIGN PATENT DOCUMENTS

| | | | |
|---|---|---|---|
| CN | 102421761 A | 4/2012 | |
| CN | 103458877 A | 12/2013 | |
| JP | 2014-501770 A | 1/2014 | |
| RU | 2526253 C2 | 8/2014 | |
| WO | 2010/128659 A1 | 11/2010 | |
| WO | WO-2010128659 A1 * | 11/2010 | ........... C07D 239/48 |
| WO | 2012/093161 A1 | 7/2012 | |
| WO | 2015/119122 A1 | 8/2015 | |

OTHER PUBLICATIONS

Nakai, Yoshinobu, "Relationship between Powder Characteristics and the Pharmaceutical Preparations," (and English Commentary), J. Society of Powder Technology (1988), vol. 25 (6), pp. 388-394 and pp. 1-17. (Year: 1988).*
Nakai, Y., "Relationship between powder characteristics and the pharmaceutical preparations," Journal of the Society of Powder Technology, Japan, 1988, vol. 25, No. 6, pp. 392-393.
Japan Patent Office—International Search Report; PCT/JP2016/069615; dated Aug. 16, 2016.
European Patent Office; Extended European Search Report in EP Application No. 16821324.7; dated Jan. 25, 2019.
Thai Patent Office; Thai Patent Application No. 1701007888 PCT; First Office Action dated Jan. 22, 2019.
First Office Action in Indonesian Application No. P00201800751 (dated Apr. 6, 2020).
Communication Pursuant to Article 94(3) EPC in European Application No. 16 821 324.7 (Dec. 12, 2019).
First Office Action in Mexican Application No. MX/a/2017/016862 (dated Feb. 28, 2020).
L.Y. Galichet, "Cellulose, Microcrystalline," in Handbook of Pharmaceutical Excipients, 5th ed. (Raymond C. Rowe et al., eds.), pp. 132-135 (2006).
S. Edge et al., "Lactose, Anhydrous," in Handbook of Pharmaceutical Excipients, 5th ed. (Raymond C. Rowe et al., eds.), pp. 385-388 (2006). S. Edge et al., "Lactose, Monohydrate," in Handbook of Pharmaceutical Excipients, 5th ed. (Raymond C. Rowe et al., eds.), pp. 389-395 (2006).
N.A. Armstrong, "Mannitol," in Handbook of Pharmaceutical Excipients, 5th ed. (Raymond C. Rowe et al., eds.), pp. 449-453 (2006).
M.C. Gohel, "A Review of Co-Processed Directly Compressible Excipients," 8(1) J. Pharm. Pharmaceut Sci 76-93 (Apr. 2005).
Office Action with Search Report in Russian Application No. 2018103354/04 (dated Nov. 28, 2019).

(Continued)

*Primary Examiner* — Craig D Ricci
*Assistant Examiner* — Janet L. Coppins
(74) *Attorney, Agent, or Firm* — Venable LLP

(57) ABSTRACT

Provided is a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide (hereinafter referred to as compound A) or a pharmaceutically acceptable salt thereof, wherein the generation of related substances during storage is inhibited. In the stable pharmaceutical composition for oral administration, the proportion of crystals of compound A or a pharmaceutically acceptable salt thereof is 60% or more with respect to the total amount of compound A or a pharmaceutically acceptable salt thereof.

11 Claims, No Drawings

(56) References Cited

OTHER PUBLICATIONS

First Office Action in Chinese Application No. 201680039513.0 (dated Mar. 20, 2020).
Notice of Reasons for Rejection in Japanese Application No. 2017-077939 (dated May 12, 2020).
First Substantive Examination Report in Philippine Application No. 1/2017/502252 (dated Jul. 9, 2020).

\* cited by examiner

STABLE PHARMACEUTICAL COMPOSITION FOR ORAL ADMINISTRATION

CROSS-REFERENCE TO RELATED APPLICATIONS

The present application is a § 371 National phase application of PCT/JP2016/069615, filed Jul. 1, 2016, which application claims priority to Japanese Patent Application No. 2015-134817, filed Jul. 3, 2015, the disclosures of which are hereby incorporated by reference in their entireties for all purposes.

TECHNICAL FIELD

The present invention relates to a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof.

BACKGROUND ART

6-Ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide (hereinafter referred to as compound A in some cases) is a compound represented by the following chemical structural formula. It has been reported that Compound A or a pharmaceutically acceptable salt thereof has, for example, an inhibitory activity of a kinase activity of an EML4 (Echinoderm microtubule associated protein like-4)-ALK (Anaplastic lymphoma kinase) fusion protein, and is useful as an active ingredient of a pharmaceutical composition for treating cancer (Patent literature 1).

[Chem. 1]

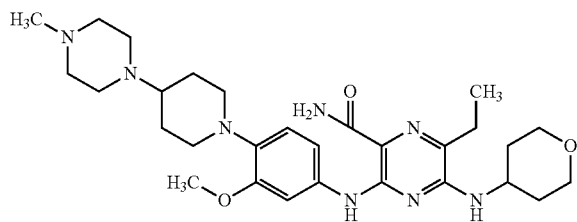

From the viewpoint of the safety of the patients, it is desirable that the generation of related substances is inhibited during storage of a formulation. For example, the Ministry of Health, Labor and Welfare in Japan published a specification of drug products, namely, the concept of related substances (impurities) in drug products as observed during stability tests (Pharmaceutical and Food Safety Bureau, Evaluation and Licensing Division Notification No. 0624001 "Revision of the Guideline on the Impurities in the Medicinal Products with New Active Ingredients"). According to the revised guideline, for example, when the amount of the drug substance to be administered per day is 10 mg to 100 mg, the threshold of related substances requiring safety qualification in a drug product is the lower of either 0.5% as the percentage of the related substances contained in the drug substance or 200 µg as the total daily intake of the related substances. Therefore, it is useful to provide a stable formulation comprising Compound A or a pharmaceutically acceptable salt thereof, in which the generation of related substances during storage is inhibited.

CITATION LIST

Patent Literature

[Patent literature 1] WO 2010/128659

SUMMARY OF INVENTION

Technical Problem

An object of the present invention is to provide a stable pharmaceutical composition for oral administration comprising Compound A or a pharmaceutically acceptable salt thereof, wherein the generation of related substances during storage is inhibited.

Solution to Problem

Compound A hemifumarate is stable in heat and humidity alone, and an increase in related substances was not observed under certain storage conditions, such as a severity test, or the like, of medicinal products. However, when the pharmaceutical composition of Comparative Example 1 described below was prepared, in accordance with an embodiment of a wet granulation method, a high shear granulation method, by granulating Compound A hemifumarate together with microcrystalline cellulose and the like, which did not cause a incompatibility with Compound A hemifumarate, using water, and drying the granulated product to make a formulation, it was found that related substances unexpectedly increased. In order to inhibit the generation of related substances of Compound A during storage, the inventors conducted intensive studies, and as a result, found that the generation of related substances of Compound A could be inhibited by inhibiting a decrease in the proportion of crystals of Compound A hemifumarate during the formulation step, and completed the present invention.

The present invention provides:

[1] a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, wherein the proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof is 60% or more with respect to the total amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof;

[2] the pharmaceutical composition for oral administration of [1], wherein the percentage of a related substance of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide is 0.20% or less, after storage of the pharmaceutical composition for oral administration under opened conditions of 40° C. and 75% relative humidity for 1 month;

[3] the pharmaceutical composition for oral administration of [1] or [2], further comprising a pharmaceutical additive capable of controlling a water content in a formulation;

[4] the pharmaceutical composition for oral administration of [3], wherein the pharmaceutical additive capable of controlling a water content in a formulation is sugars and/or sugar alcohols;

[5] the pharmaceutical composition for oral administration of [4], wherein the sugars and/or sugar alcohols are lactose and/or D-mannitol;

[6] the pharmaceutical composition for oral administration of any one of [3] to [5], wherein the content of the pharmaceutical additive capable of controlling a water content in a formulation is 20% by weight to 90% by weight with respect to the total weight of the pharmaceutical composition for oral administration;

[7] a method of manufacturing a stable pharmaceutical composition for oral administration, said method comprising:
(1) mixing 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof with a pharmaceutical additive capable of controlling a water content in a formulation,
(2) granulating the mixture so that the proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof is 60% or more with respect to the total amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, and
(3) compression-molding the granulated product;

[8] the method of manufacturing a pharmaceutical composition for oral administration of [7], wherein the granulation is carried out at a water content of the granulated product of 30% or less;

[9] the method of manufacturing a pharmaceutical composition for oral administration [7] or [8], wherein the pharmaceutical additive capable of controlling a water content in a formulation is sugars and/or sugar alcohols;

[10] a method of stabilizing 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, in a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, by setting the proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof with respect to the total amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof to 60% or more, and/or by adding a pharmaceutical additive capable of controlling a water content in a formulation;

[11] use of a pharmaceutical additive capable of controlling a water content in a formulation in the manufacture of a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof;

[12] a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, and lactose and/or D-mannitol; and

[13] a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, and D-mannitol.

Advantageous Effects of Invention

According to the present invention, a stable pharmaceutical composition for oral administration comprising Compound A or a pharmaceutically acceptable salt thereof, wherein the generation of related substances during storage is inhibited, can be provided.

DESCRIPTION OF EMBODIMENTS

The term "stable" as used herein means to have stability against, for example, heat, light, temperature, and/or humidity. For example, after a pharmaceutical composition for oral administration is allowed to stand under the following conditions, it is defined as an embodiment in which related substances of Compound A contained in the pharmaceutical composition for oral administration is a specific percentage or less. For example, after a pharmaceutical composition for oral administration is allowed to stand at 70° C. for 9 days, at 40° C. and 75% relative humidity (hereinafter X % relative humidity is sometimes abbreviated as X % RH) for 6 months in an embodiment, at 40° C. and 75% RH for 3 months in an embodiment, at 40° C. and 75% RH for 1 month in an embodiment, at 25° C. and 60% RH for 12 months in an embodiment, at 25° C. and 60% RH for 6 months in an embodiment, at 25° C. and 60% RH for 3 months in an embodiment, and at 25° C. and 60% RH for 1 month in an embodiment, it is defined as the percentage of related substances of Compound A contained in the pharmaceutical composition for oral administration measured by a high-performance liquid chromatographic method (hereinafter sometimes abbreviated as an HPLC method) being, for example, 0.50% or less, 0.20% or less in an embodiment, and 0.10% or less in an embodiment. In an embodiment, after a pharmaceutical composition for oral administration is allowed to stand under opened conditions of 40° C. and 75% RH for 1 month, 3 months, or 6 months, it is defined as the percentage of related substances of Compound A contained in the pharmaceutical composition for oral administration measured by an HPLC method being, for example, 0.20% or less, and 0.10% or less in an embodiment.

The term "related substance of Compound A" is defined as, for example, an oxidative decomposition product of Compound A, and in an embodiment, a substance having a relative retention time of about 1.06 with respect to the peak of Compound A, as measured by the HPLC method described below. In connection with this, the related substance having a relative retention time of about 1.06 with respect to the peak of Compound A is presumed to be an oxidative decomposition product of Compound A. Numerical values used are interpreted as larger variable values, in general, within an experimental error (for example, within the 95% confidence interval for the mean), or within ±10% of the indicated value, and all the values of the variable.

The "proportion of crystals" of Compound A or a pharmaceutically acceptable salt thereof is defined as the proportion of crystals with respect to the total amount of Compound A or a pharmaceutically acceptable salt thereof, and can be calculated by near-infrared spectroscopy (NIR), as described below, or the like.

The term "loss on drying" as used herein means the amount of moisture that is contained in a sample and lost by drying. The loss on drying can be calculated, for example, by the following equation:

Loss on drying (%)=(weight (mass) reduced by drying/weight (mass) of a sample at the beginning of the measurement of loss on drying)×100

More particularly, the loss on drying can be calculated by the following equation:

Loss on drying (%)=[(weight (mass) of a sample at the beginning of the measurement of loss on drying−weight (mass) of a sample at the end of the measurement of loss on drying)/(weight (mass) of a sample at the beginning of the measurement of loss on drying)]×100

Compound A or a pharmaceutically acceptable salt thereof, which is used in the present invention, is easily available, for example, by a method described in Patent literature 1, or in a similar fashion to that.

Compound A may be in a free form, which does not form a salt, and may form a pharmaceutically acceptable salt with an acid. Examples of such a salt include an acid addition salt with an inorganic acid, such as hydrochloric acid, hydrobromic acid, hydroiodic acid, sulfuric acid, nitric acid, phosphoric acid, or the like; and an acid addition salt with an organic acid, such as formic acid, acetic acid, propionic acid, oxalic acid, malonic acid, succinic acid, fumaric acid, hemifumaric acid, maleic acid, lactic acid, malic acid, citric acid, tartaric acid, carbonic acid, picric acid, methanesulfonic acid, ethanesulfonic acid, glutamic acid, or the like. These salts can be prepared by conventional methods. Hemifumarate may be exemplified in an embodiment.

Compound A or a pharmaceutically acceptable salt thereof exhibits, for example, an inhibitory activity of a kinase activity of an EML4-ALK fusion protein, and is useful as an active ingredient of a pharmaceutical composition for the treatment of cancer.

The dose of compound A or a pharmaceutically acceptable salt thereof can be appropriately determined depending on individual cases taken into consideration, for example, symptoms, age of the patient, sex, or the like.

For ordinary oral administration, the daily dosage for an adult is suitably 0.001 mg/kg or more to 100 mg/kg or less, preferably 0.005 mg/kg to 30 mg/kg, and more preferably 0.01 mg/kg to 10 mg/kg. This is administered in one dose, or divided into two to four doses per day.

The content of Compound A or a pharmaceutically acceptable salt thereof is, for example, with respect to the weight of a pharmaceutical composition for oral administration, 1% by weight or more to 70% by weight or less, 5% by weight or more to 50% by weight or less in an embodiment, and 10% by weight or more to 40% by weight or less in an embodiment. The amount contained of Compound A or a pharmaceutically acceptable salt thereof is, in the whole formulation, 1 mg or more to 200 mg or less, 5 mg or more to 150 mg or less in an embodiment, and 40 mg or more to 50 mg or less in an embodiment.

The proportion of crystals of Compound A or a pharmaceutically acceptable salt thereof, which are used in the present invention, is not particularly limited, so long as it is within a range where Compound A or a pharmaceutically acceptable salt thereof is stable during storage. The proportion of the crystals can be calculated by, for example, a differential scanning calorimeter analysis (DSC analysis) method, a powder X-ray diffraction method, a solid-state NMR method, a near-infrared spectroscopy (NIR) method, or the like.

As a method of calculating the proportion of crystals of Compound A hemifumarate in Compound A hemifumarate, for example, the spectrum is measured, as a near-infrared spectroscopy measurement, by a Fourier transform near-infrared spectrometer (MPA, Bruker Optics K.K.)(measurement range; 12500 $cm^{-1}$ to 5800 $cm^{-1}$, resolution; 8 $cm^{-1}$, number of scans; 32), and the obtained spectrum is secondary-differentiated (Savitzky-Golay convolution method), and can be analyzed using a near-infrared spectrum analysis software (for example, OPUS, Bruker Optics K.K.). The pharmaceutical composition for oral administration is powdered using a mortar and pestle to measure the spectrum. Before the spectrum measurement of the pharmaceutical composition for oral administration, spectra of preparations, in which crystals of Compound A hemifumarate are mixed in various proportions, are regression-analyzed by a partial least square method to create a calibration curve, and each spectrum obtained from the pharmaceutical composition for oral administration is interpolated into the calibration curve to calculate the proportion of crystals of Compound A hemifumarate.

The proportion of the crystals is, for example, with respect to the total amount of Compound A or a pharmaceutically acceptable salt thereof, 60% or more, 60% or more to 100% or less in an embodiment, 70% or more to 100% or less in an embodiment, 80% or more to 100% or less in an embodiment, 90% or more to 100% or less in an embodiment, 60% or more to less than 100% in an embodiment, 70% or more to less than 100% in an embodiment, 80% or more to less than 100% in an embodiment, and 90% or more to less than 100% in an embodiment. In connection with this, numerical values used are interpreted as a larger variable value, in general, within an experimental error (for example, within the 95% confidence interval for the mean), or within ±10% of the indicated value, and all the values of the variable.

The pharmaceutical composition for oral administration of the present invention can further comprise a pharmaceutical additive capable of controlling a water content during a formulation step and/or storage (hereinafter sometimes referred to as a pharmaceutical additive capable of controlling a water content in a formulation). The pharmaceutical additive capable of controlling a water content in a formulation is not particularly limited, so long as the additive per se exhibits loss on drying capable of keeping the composition comprising Compound A or a pharmaceutically acceptable salt thereof stable; or a stable pharmaceutical composition for oral administration comprising Compound A or a pharmaceutically acceptable salt thereof can be provided by keeping the water content of the composition comprising Compound A or a pharmaceutically acceptable salt thereof during a formulation step (in particular, a granulation step) low, or by further reducing the water content in the formulation and maintaining the water content. Examples of the additive include sugars and/or sugar alcohols, and the additive is D-mannitol, maltose, maltitol, erythritol, xylitol, lactose (lactose hydrate), sucrose, glucose, sorbitol, trehalose, lactitol, fructose, arabinose, or trehalose in an embodiment, lactose (lactose hydrate) or D-mannitol in an embodiment, and D-mannitol in an embodiment.

The loss on drying of the pharmaceutical additive capable of controlling a water content in a formulation can be measured, for example, in a similar manner to the Loss on Drying Test, as defined in the General Tests of The Japanese Pharmacopoeia, Sixteenth Edition. In an embodiment, the loss on drying can be measured by allowing the pharmaceutical additive to stand under predetermined temperature and humidity conditions to moisturize it until the weight (mass) reaches a constant weight (mass), and then by drying it under predetermined temperature and humidity conditions until the weight (mass) reaches a constant weight (mass). In an embodiment, the loss on drying of a pharmaceutical additive, as measured by putting the pharmaceutical additive into a bottle, allowing the bottle to stand under opened conditions of 40° C. and 75% RH for 1 week, and measuring the loss on drying after storage by the loss on drying test (for example, HR73 Halogen Moisture Analyzer (manufactured by METTLER TOLEDO) is used as an apparatus, and the measurement is carried out until the weight of the sample reaches a constant weight at 80° C.) is, for example, 20% or less, 1.0% or less in an embodiment, 0.5% or less in an embodiment, and 0.4% or less in an embodiment.

The loss on drying of a pharmaceutical composition (for example, a tablet) can be measured, for example, in a similar manner to the Loss on Drying Test, as defined in the General Tests of The Japanese Pharmacopoeia, Sixteenth Edition. In an embodiment, the loss on drying can be measured by allowing the pharmaceutical composition (for example, a tablet) to stand under predetermined temperature and humidity conditions to moisturize it until the weight (mass) reaches a constant weight (mass), and then by drying it under predetermined temperature and humidity conditions until the weight (mass) reaches a constant weight (mass). In an embodiment, the loss on drying of a pharmaceutical composition (for example, a tablet), as measured by putting the pharmaceutical composition (for example, a tablet) into a bottle, allowing the bottle to stand under opened conditions of 40° C. and 75% RH for 1 week, and measuring the loss on drying after storage by the loss on drying test (for example, HR73 Halogen Moisture Analyzer (manufactured by METTLER TOLEDO) is used as an apparatus, and the measurement is carried out until the weight of the sample reaches a constant weight at 80° C.) is, for example, 4.0% or less, 3.0% or less in an embodiment, and 2.0% or less in an embodiment.

The pharmaceutical additive capable of controlling a water content in a formulation may be appropriately added alone, or as a combination of two or more, in appropriate amounts.

The content is, with respect to the total weight of the pharmaceutical composition for oral administration, for example, 20% by weight or more to 90% by weight or less, 30% by weight or more to 80% by weight or less in an embodiment, 40% by weight or more to 70% by weight or less in an embodiment, 50% by weight or more to 70% by weight or less in an embodiment, and 50% by weight or more to 60% by weight or less in an embodiment.

The pharmaceutical composition for oral administration of the present invention may be various formulations, such as tablets, capsules, powders, granules, fine granules, dry syrups, or the like. It is a tablet or a capsule in an embodiment, and a tablet in an embodiment.

In the pharmaceutical composition for oral administration of the present invention, various pharmaceutical additives, such as binders, disintegrating agents, corrigents, effervescent agents, sweeteners, flavors, lubricants, buffers, antioxidants, stabilizers, surfactants, film coating agents, and the like, may be appropriately used, if desired, to the extent that the effects of the present invention can be achieved.

Examples of the binders include gum arabic, hypromellose, hydroxypropyl cellulose, hydroxyethyl cellulose, and the like Examples of the disintegrating agents include corn starch, potato starch, carmellose calcium, carmellose sodium, low substituted hydroxypropyl cellulose, and the like.

Examples of the corrigents include citric acid, tartaric acid, malic acid, and the like.

Examples of the effervescent agents include sodium bicarbonate, and the like.

Examples of the sweeteners include saccharin sodium, glycyrrhizic acid, aspartame, stevia, thaumatin, and the like.

Examples of the flavors include lemon, lemon-lime, orange, menthol, and the like.

Examples of the lubricants include magnesium stearate, calcium stearate, and the like.

Examples of the buffers include citric acid, succinic acid, fumaric acid, tartaric acid, ascorbic acid, and salts thereof; glutamic acid, glutamine, glycine, aspartic acid, alanine, arginine, and salts thereof; magnesium oxide, zinc oxide, magnesium hydroxide, phosphoric acid, boric acid, and salts thereof; and the like.

Examples of the antioxidants include citric acid, sodium nitrite, ascorbic acid, L-ascorbic acid stearate ester, sodium hydrogen nitrite, sodium sulfite, α-thioglycerin, sodium edetate, erythorbic acid, cysteine hydrochloride, dried sodium sulfite, potassium dichloroisocyanurate, soybean lecithin, sodium thioglycolate, sodium thiomalate, natural vitamin E, tocopherol, d-δ-tocopherol, tocopherol acetate ester, mixed tocopherols concentrate, ascorbic acid palmitate, sodium pyrosulfite, butylhydroxyanisole, 1,3-butylene glycol, benzotriazole, pentaerythrityl-tetrakis[3-(3,5-di-t-butyl-4-hydroxyphenyl)propionate], 2-mercaptobenzimidazole, propyl gallate, dibutylhydroxytoluene, and the like.

The antioxidants also function as stabilizers. Examples of the stabilizers include citric acid; and citric acid hydrate, calcium citrate, sodium citrate hydrate, sodium dihydrogen citrate, disodium citrate, and the like in an embodiment.

Examples of the surfactants include polysorbate 80, sodium lauryl sulfate, polyoxyethylene hydrogenated castor oil, and the like.

Examples of the film coating agents include hypromellose, polyvinyl alcohol, and the like.

These pharmaceutical additives may be appropriately added alone, or as a combination of two or more, in appropriate amounts. With respect to the contents of the pharmaceutical additives, each pharmaceutical additive may be used in an amount such that the desired effects of the present invention may be achieved.

The pharmaceutical composition for oral administration of the present invention can be produced by known methods comprising the steps of, for example, pulverization, mixing, granulation, drying, molding (tableting), film coating, crystallization, and the like. The method of manufacturing a pharmaceutical composition for oral administration of the present invention will be explained below.

Pulverization Step and Mixing Step

In the pulverization step, both the apparatus and the means are not particularly limited, so long as it is a method in which Compound A or a pharmaceutically acceptable salt thereof and appropriate pharmaceutical additives can be pulverized in an ordinary pharmaceutical manner. Examples of a pulverizer include a hammer mill, a ball mill, a jet mill, a colloid mill, and the like. The conditions for pulverization may be appropriately selected and are not particularly limited.

In the step of mixing components subsequent to the pulverization step, both the apparatus and the means are not particularly limited, so long as it is a method in which the components can be uniformly mixed in an ordinary pharmaceutical manner.

Granulation Step

In the granulation step, both the apparatus and the means are not particularly limited, so long as it is a method in which Compound A or a pharmaceutically acceptable salt thereof and appropriate pharmaceutical additives can be granulated in an ordinary pharmaceutical manner.

Examples of a granulation method and a granulation apparatus, which are used in a wet granulation using a solvent such as water, include a high shear granulation method, a milling (pulverization) granulation method, a fluidized bed granulation method, an extrusion granulation method, a tumbling granulation method, and a spray granulation method; and apparatuses and the like, which are used in these methods. A fluidized bed granulation method and a fluidized bed granulator are preferable, and a drying method is not particularly limited, so long as it can be dried in an ordinary pharmaceutical manner.

During granulation, it is preferable that the water content is low in order to inhibit a decrease in the proportion of crystals of Compound A or a pharmaceutically acceptable salt thereof. The water content during granulation is, for example, 30% or less, 5% or less in an embodiment, 3% or less in an embodiment, 2% or less in an embodiment, and 1% or less in an embodiment. The granulation method is not particularly limited, so long as the water content can be controlled within the range. Examples of such a granulation method include a milling (pulverization) granulation method, a fluidized bed granulation method, a tumbling granulation method, and a spray granulation method; and a fluidized bed granulation method in an embodiment.

The water content can be measured, for example, by a loss on drying method, or the like. As an apparatus, for example, a halogen moisture analyzer (METTLER TOLEDO) may be used.

A high shear granulation method can be selected, when conditions capable of reducing the water content in granules during granulation are used.

As a method not using water during granulation, a wet granulation method using a non-aqueous solvent, or a dry granulation method, can also be used.

Drying Step

In the drying step, both the apparatus and the means are not particularly limited, so long as it is a method in which the granulated product can be dried in an ordinary pharmaceutical manner. Examples of the apparatus include a forced-air dryer, a dryer under reduced pressure, a vacuum dryer, a fluidized bed granulation dryer, and the like.

After drying, the dried product may be sieved and sized using a sieve, a comil, or the like, if desired.

Molding Step

In the molding step, both the apparatus and the means are not particularly limited, so long as it is a method of molding the pharmaceutical composition for oral administration of the present invention. Examples of the method include a method in which, without the granulation and drying step, Compound A or a pharmaceutically acceptable salt thereof and appropriate pharmaceutical additives are mixed, and directly compression-molded to prepare the pharmaceutical composition for oral administration; a method in which Compound A or a pharmaceutically acceptable salt thereof and appropriate pharmaceutical additives are granulated and dried, and compression-molded to prepare the pharmaceutical composition for oral administration; a method in which Compound A or a pharmaceutically acceptable salt thereof and appropriate pharmaceutical additives are granulated, and further mixed with a lubricant, and the mixture is compression-molded to prepare the pharmaceutical composition for oral administration; and the like.

Examples of a tableting machine include a rotary tableting machine, an oil press, and the like.

The conditions for tableting, such as tableting pressure, are not particularly limited, so long as it is tableting pressure capable of compression-molding.

The hardness of the tableted product is not particularly limited, so long as it is not damaged during the manufacturing process, the distribution process, and the like. The hardness may be, for example, 40 to 200 N.

Film Coating Step

After tableting, the surface of the pharmaceutical composition for oral administration may be film coated.

The method of film coating is not particularly limited, so long as it may be coated in an ordinary pharmaceutical manner. Examples of the coating include pan coating, dip coating, and the like.

A film coating agent may be appropriately added alone, or as a combination of two or more, in appropriate amounts.

The coating rate is not particularly limited, so long as a film can be formed. The coating rate is, for example, with respect to the total weight of the pharmaceutical composition for oral administration, 1% by weight to 10% by weight, or the like.

During film coating or after film coating, the coated product may be dried. The drying method is not particularly limited, so long as it may be dried in an ordinary pharmaceutical manner. The conditions for drying are not particularly limited, so long as they are appropriately selected in view of, for example, the stability of the pharmaceutical composition for oral administration.

Crystallization Step

When the proportion of crystals of Compound A or a pharmaceutically acceptable salt thereof is reduced, a step of promoting crystallization may be adopted. Examples of the step include a microwave irradiation treatment, an ultrasonic irradiation treatment, a low frequency irradiation treatment, a thermal electron irradiation treatment, and the like.

As the microwave irradiation treatment, for example, a wavelength of 10 MHz to 25 GHz may be irradiated. Although the treatment time depends on the degree of an initial crystal proportion, or pharmaceutical additive components, it is performed, for example, for 10 seconds to 60 minutes. The irradiation may be continuous or intermittent, and at any time.

As the ultrasonic irradiation treatment, for example, sound waves with a frequency of 10 kHz to 600 kHz may be irradiated. Although the treatment time depends on the degree of a crystal proportion, or pharmaceutical additive components, it is performed, for example, for 10 seconds to 24 hours. The irradiation may be continuous or intermittent, and at any time.

The present invention includes a method of stabilizing Compound A or a pharmaceutically acceptable salt thereof by the proportion of crystals of Compound A or a pharmaceutically acceptable salt thereof, and/or by a pharmaceutical additive capable of controlling a water content in a formulation.

The present invention includes a use of a pharmaceutical additive capable of controlling a water content in a formulation, in the manufacture of a stable pharmaceutical composition for oral administration comprising Compound A or a pharmaceutically acceptable salt thereof.

With respect to "crystals of Compound A or a pharmaceutically acceptable salt thereof", "a pharmaceutical additive capable of controlling a water content in a formulation" and "Compound A or a pharmaceutically acceptable salt thereof", which are used in the stabilizing method of the present invention, and the use of a pharmaceutical additive capable of controlling a water content in a formulation of the present invention, the explanations therefor described in the pharmaceutical composition for oral administration of the present invention can be directly applied.

With respect to the content of each component, their blending method, and the like in the stabilizing method of the present invention, and the use of a pharmaceutical additive capable of controlling a water content in a formulation of the present invention, the explanations therefor described in the pharmaceutical composition for oral administration of the present invention and the method of producing the same can be directly applied.

EXAMPLES

The present invention will now be further illustrated by, but is by no means limited to, the following Comparative Examples, Examples, and Experimental Examples.

Comparative Example 1 and Examples 1 to 3

The formulations of Comparative Example 1 and Examples 1 to 3 are shown in Tables 1 and 2. Compound A hemifumarate, which was used below, had been prepared in accordance with a method described in WO 2010/128659, or in a similar fashion to that.

TABLE 1

|  | Comparative Example 1 | Example 1 |
|---|---|---|
| Compound A hemifumarate | 11.05 | 44.2 |
| Lactose hydrate | 53.75 | 215.0 |
| Microcrystalline cellulose | 4.5 | 18.0 |
| Low-substituted hydroxypropyl cellulose | 9.0 | 36.0 |
| Hydroxypropyl cellulose | 1.8 | 7.2 |
| Microcrystalline cellulose | 4.5 | 18.0 |
| Low-substituted hydroxypropy cellulose | 4.5 | 18.0 |
| Magnesium stearate | 0.9 | 3.6 |
| Subtotal | 90.0 | 360.0 |
| Film-coating agent (Opadry 03F42203) | 2.7 | 10.8 |
| Total | 92.7 | 370.8 |

Unit: mg

TABLE 2

|  | Example 2 | Example 3 |
|---|---|---|
| Compound A hemifumarate | 44.2 | 44.2 |
| D-mannitol | 82.5 | 86.12 |
| Hydroxypropyl cellulose | 4.2 | 4.32 |
| Low-substituted hydroxypropyl cellulose | 7.0 | 7.2 |
| Magnesium stearate | 2.1 | 2.16 |
| Subtotal | 140.0 | 144.0 |
| Film-coating agent (Opadry 03F42203) | 4.2 | 4.3 |
| Total | 144.2 | 148.3 |

Unit: mg

Pharmatose 200M (product name, manufactured by FrieslandCampina DMV BV) was used as lactose hydrate, HPC-L (product name, manufactured by Nippon Soda Co., Ltd.) was used as hydroxypropyl cellulose, Parteck LUB MST (product name, manufactured by Merck KGaA) was used as magnesium stearate, and PEARLITOL 50C (product name, manufactured by ROQUETTE) was used as D-mannitol.

Comparative Example 1

In accordance with the formulation described in Table 1, 110.5 g of Compound A hemifumarate, 537.5 g of lactose hydrate, 45 g of microcrystalline cellulose (product name: Ceolus PH-101, manufactured by Asahi Kasei Chemicals Corporation), 90 g of low-substituted hydroxypropyl cellulose (product name: L-HPC LH-21, manufactured by Shin-Etsu Chemical Co., Ltd.), and 18 g of hydroxypropyl cellulose were mixed using a high shear granulator (product name: VG-05, manufactured by Powrex Corporation), and 300 g of purified water was further added thereto, and the mixture was granulated. The water content of the granulated product during granulation was 27%. Two additional lots of granulation were performed, and the granulated product was obtained by drying for 15 hours using a vacuum dryer (product name: DB-30, manufactured by ULVAC, Inc.). After 2403 g of the obtained granulated product was sieved, 135 g of microcrystalline cellulose (product name: Ceolus PH-102, manufactured by Asahi Kasei Chemicals Corporation), 135 g of low-substituted hydroxypropyl cellulose (product name: L-HPC LH-11, manufactured by Shin-Etsu Chemical Co., Ltd.), and 27 g of magnesium stearate were added thereto, and mixed using a mixer (product name: Container Mixer LM20, manufactured by Kotobuki Industries Co., Ltd.) to obtain a mixed product (granules for tablet compression). The obtained mixed product was formed into tablets using a rotary tableting machine (product name: HT-X20, manufactured by HATA TEKKOSHO Co., Ltd.) to obtain tablets (uncoated tablets). The obtained uncoated tablets (1350 g) were film coated using a film coating machine (product name: HCT-30, manufactured by Freund Corporation) with a liquid, prepared by dissolving/dispersing OPADRY 03F42203 (product name, manufactured by Colorcon) in purified water, so that the concentration of OPADRY 03F42203 was 10% by weight in total (concentration of solid components). An additional lot of film coating was performed, to obtain tablets (film coated tablets) of Comparative Example 1.

Example 1

In accordance with the formulation described in Table 1, 442 g of Compound A hemifumarate, 2150 g of lactose hydrate, 180 g of microcrystalline cellulose (product name: Ceolus PH-101, manufactured by Asahi Kasei Chemicals Corporation), 360 g of low-substituted hydroxypropyl cellulose (product name: L-HPC LH-21, manufactured by Shin-Etsu Chemical Co., Ltd.), and 72 g of hydroxypropyl cellulose were mixed using a high shear granulator (product name: VG-25, manufactured by Powrex Corporation), and the mixture was granulated by adding 1170 g of purified water. The water content of the granulated product during granulation was 27%. Nine additional lots of granulation were performed, and the granulated product was obtained by drying for 1 hour using a fluidized bed granulation dryer (product name: GPCG-PRO-5, manufactured by Powrex Corporation). After 32040 g of the obtained granulated product was sieved, 1800 g of microcrystalline cellulose (product name: Ceolus PH-102, manufactured by Asahi Kasei Chemicals Corporation), 1800 g of low-substituted hydroxypropyl cellulose (product name: L-HPC LH-11, manufactured by Shin-Etsu Chemical Co., Ltd.), and 360 g of magnesium stearate were added thereto, and mixed using a mixer (product name: Container Mixer PM200, manufactured by Kotobuki Industries Co., Ltd.) to obtain a mixed product (granules for tablet compression). The obtained mixed product was formed into tablets using a rotary tableting machine (product name: HT-CVX-TYPEIII20, manufactured by HATA TEKKOSHO Co., Ltd.) to obtain tablets (uncoated tablets). The obtained uncoated tablets (36000 g) were film coated using a film coating machine (product name: PRC-20/60, manufactured by Powrex Corporation) with a liquid, prepared by dissolving/dispersing OPADRY 03F42203 (product name, manufactured by Colorcon) in purified water, so that the concentration of OPADRY 03F42203 was 10% by weight in total (concentration of solid components), to obtain tablets (film coated tablets) of Example 1.

Example 2

In accordance with the formulation described in Table 2, 6630 g of Compound A hemifumarate and 12375 g of D-mannitol were mixed using a fluidized bed granulation dryer (product name: GPCG-PRO-15, manufactured by Powrex Corporation). After mixing, the mixture was granulated by spraying 9000 g of a hydroxypropyl cellulose aqueous solution (solid content: 7% by weight) as a binder, and dried to obtain a granulated product. The water content of the granulated product during granulation was 0.43% at the maximum. After 19635 g of the obtained granulated product was sieved, 1050 g of low-substituted hydroxypropyl cellulose (product name: L-HPC LH-21, manufactured by Shin-Etsu Chemical Co., Ltd.) and 315 g of magnesium stearate were added thereto, and mixed using a mixer (product name: Container Mixer PM200, manufactured by Kotobuki Industries Co., Ltd.) to obtain a mixed product (granules for tablet compression). The obtained mixed product was formed into tablets using a rotary tableting machine (product name: HT-CVX-TYPEIII20, manufactured by HATA TEKKOSHO Co., Ltd.) to obtain tablets (uncoated tablets). The obtained uncoated tablets (21000 g) were film coated using a film coating machine (product name: PRC-20/60, manufactured by Powrex Corporation) with a liquid, prepared by dissolving/dispersing OPADRY 03F42203 (product name, manufactured by Colorcon) in purified water, so that the concentration of OPADRY 03F42203 was 10% by weight in total (concentration of solid components), to obtain tablets (film coated tablets) of Example 2.

Example 3

Tablets (film coated tablets) of Example 3 were prepared in a similar manner to that of Example 2, in accordance with the formulation described in Table 2.

Experimental Example 1: Calculation of Proportion of Crystals

With respect to the tablets (film coated tablets) prepared in Comparative Example 1, Example 1, Example 2, and Example 3, the proportion of crystals of Compound A hemifumarate after production was calculated by near-infrared spectroscopy.

More particularly, the spectrum was measured by a Fourier transform near-infrared spectrometer (product name: MPA, Bruker Optics K.K.)(measurement range; 12500 $cm^{-1}$ to 5800 $cm^{-1}$, resolution; 8 $cm^{-1}$, number of scans; 32), and the obtained spectrum was secondary-differentiated (Savitzky-Golay convolution method), and analyzed using a near-infrared spectrum analysis software (product name: OPUS, Bruker Optics K.K.). The tablets were powdered using a mortar and pestle, and the spectra were measured. Before the spectrum measurement of the tablets, spectra of preparations, in which crystals of Compound A hemifumarate were mixed in various proportions, were regression-analyzed by a partial least square method to create a calibration curve, and each spectrum obtained from the tablets was interpolated into the calibration curve to calculate the proportion of crystals of Compound A hemifumarate. The results are shown in Table 4.

Experimental Example 2: Measurement of Related Substances

The tablets (film coated tablets) prepared in Comparative Example 1, Example 1, Example 2, and Example 3 were put into bottles, and allowed to stand under opened conditions of 40° C. and 75% RH for 1 month and 3 months. Related substances after storage were measured by an HPLC method. The measurement of related substances was carried out under the following conditions:

As an HPLC column, Kinetex XB-C18, particle size: 2.6 μm, 4.6 mm (inner diameter)×75 mm (manufactured by Phenomenex Inc.), or its equivalent, was used, and maintained at 40° C.

As mobile phase A, a perchlorate solution (pH 2.2) was used, and as mobile phase B, acetonitrile was used.

As sample solutions, samples were diluted with a perchlorate solution (pH 2.2)/acetonitrile mixture (=4/1) was used, so that the concentration of compound A was 0.8 mg/mL.

As a standard solution, a standard was diluted with a perchlorate solution (pH 2.2)/acetonitrile mixture (=4/1) was used, so that the concentration of compound A was 0.008 mg/mL.

The measurement of related substances was carried out using an ultraviolet absorption spectrophotometer (wavelength: 220 nm), in accordance with the gradient program shown in Table 3 below, and the percentage of each related substance was calculated based on the ratio of the peak area of each related substance to the peak area of the standard solution.

The measurement results of a related substance having a relative retention time of about 1.06 with respect to the peak of Compound A are shown in Table 4.

TABLE 3

| Time (min.) | Mobile phase A (%) | Mobile phase B (%) |
|---|---|---|
| 0→2 | 96 | 4 |
| 2→5 | 96→85 | 4→15 |
| 5→20 | 85→68 | 15→32 |
| 20→25 | 68→30 | 32→70 |
| 25→26 | 30 | 70 |
| 26→26.1 | 30→96 | 70→4 |
| 26.1→30 | 96 | 4 |

TABLE 4

| | Proportion of crystals (%) | Related substance (%) Opened conditions of 40° C. and 75% RH | | |
|---|---|---|---|---|
| | | At the beginning of test | 1 month | 3 months |
| Comparative Example 1 | 26 | 0.05 | 0.21 | N.T. |
| Example 1 | 64 | <LOQ | 0.11 | 0.26 |
| Example 2 | 98 | <LOQ | <LOQ | N.T. |
| Example 3 | 85 | <LOQ | <LOQ | <LOQ |

LOQ: Limit of Quantitation,
N.T.: Not Tested

Comparative Example 1 was prepared by a high shear granulation method, as similar to Example 1, but they were different from each other in the proportion of crystals. It is inferred that this is due to the difference in drying time caused by different drying methods.

In the tablet of Example 1, in which the proportion of crystals of Compound A hemifumarate was 64%, the percentage of the related substance was 0.11% after storage under opened conditions of 40° C. and 75% RH for 1 month, and the percentage of the related substance was 0.26% after storage for 3 months. In the tablets of Examples 2 and 3, the percentage of the related substance after storage for 1 month was less than the limit of quantitation (LOQ). The tablets of these Examples contained a small amount of a related substance, in comparison with the tablet of the Comparative Example, and were stable. For reference, the LOQ is 0.05%.

As described above, it was confirmed that when the proportion of crystals of Compound A hemifumarate increased, the generation of related substances could be inhibited.

Examples 4 to 15

After water was added to the crystals of Compound A hemifumarate, it was dried to obtain Compound A hemifumarate, of which the proportion of crystals was 62%. Various pharmaceutical additives shown in Table 5 were physically mixed with the obtained Compound A hemifumarate at a weight ratio of 1:1, and the obtained pharmaceutical compositions were put into bottles and allowed to stand under opened conditions of 40° C. and 75% RH for 1 month and 3 months.

Experimental Example 3: Measurement of Related Substances

Related substances contained in the pharmaceutical compositions of the Examples were measured in a similar manner to that of Experimental Example 2. The measurement results of a related substance having a relative retention time of about 1.06 with respect to the peak of Compound A are shown in Table 5.

Experimental Example 4: Measurement of Loss on Drying of Pharmaceutical Additives The measurement of loss on drying of various pharmaceutical additives shown in Table 5 was carried out in a similar manner to the test for above loss on drying. The pharmaceutical additives used were lactose hydrate (product name: Pharmatose 200M, manufactured by Friesland-Campina DMV BV), hydroxypropyl cellulose (product name: HPC-L, manufactured by Nippon Soda Co., Ltd.), magnesium stearate (product name: Parteck LUB MST, manufactured by Merck KGaA), D-mannitol (product name: PEARLITOL 50C, manufactured by ROQUETTE), microcrystalline cellulose (product name: Ceolus PH-101, manufactured by Asahi Kasei Chemicals Corporation), anhydrous dibasic calcium phosphate (product name: GS, manufactured by Kyowa Chemical Industry Co., Ltd.), hypromellose (product name: TC-5E, Shin-Etsu Chemical Co., Ltd.), corn starch (product name: corn starch, manufactured by Nihon Shokuhin Kako Co., Ltd.), low-substituted hydroxypropyl cellulose (product name: L-HPC LH-21, low-substituted hydroxypropyl cellulose), croscarmellose sodium (product name: KICCOLATE ND-2HS, manufactured by Nichirin Chemical Industries, Ltd.), calcium stearate (product name: Parteck LUB CST, manufactured by Merck KGaA), and talc (product name: Hi-filler, manufactured by Matsumura Sangyo Co., Ltd.).

TABLE 5

| Number of Example | Pharmaceutical additive | Loss on drying of pharmaceutical additive (%) | 40° C. · 75% RH 1 month Amount of related substance after storage (%) | 40° C. · 75% RH 3 months Amount of related substance after storage (%) |
|---|---|---|---|---|
| Reference value | (Not added) | — | <LOQ | 0.06 |
| Example 4 | anhydrous dibasic calcium phosphate | 0.20 | <LOQ | 0.06 |
| Example 5 | Lactose hydrate | 0.26 | <LOQ | <LOQ |
| Example 6 | D-mannitol | 0.32 | <LOQ | <LOQ |
| Example 7 | Talc | 0.46 | <LOQ | 0.06 |
| Example 8 | Calcium stearate | 0.53 | <LOQ | 0.06 |
| Example 9 | Magnesium stearate | 1.5 | <LOQ | 0.09 |
| Example 10 | Microcrystalline cellulose | 7.8 | 0.06 | 0.10 |
| Example 11 | Hydroxypropyl cellulose | 9.3 | 0.05 | 0.11 |
| Example 12 | Hypromellose | 9.5 | <LOQ | 0.09 |
| Example 13 | Corn starch | 13.2 | 0.06 | 0.11 |

TABLE 5-continued

| Number of Example | Pharmaceutical additive | Loss on drying of pharmaceutical additive (%) | 40° C. · 75% RH 1 month Amount of related substance after storage (%) | 40° C. · 75% RH 3 months Amount of related substance after storage (%) |
|---|---|---|---|---|
| Example 14 | Low-substituted Hydroxypropyl cellulose | 13.4 | 0.05 | 0.11 |
| Example 15 | Croscarmellose sodium | 18.6 | 0.05 | 0.10 |

LOQ: Limit of Quantitation

It was confirmed that the pharmaceutical compositions of Examples 4 to 15 were stable after 1 month and 3 months under opened conditions of 40° C. and 75% RH, and that when the proportion of crystals of Compound A hemifumarate increased, the generation of related substances could be inhibited. It was suggested that, in particular, lactose hydrate (Example 5) and D-mannitol (Example 6) were suitable from the viewpoint of inhibition of the generation of related substances.

Experimental Example 5: Measurement of Loss on Drying of Tablets of Examples 2 and 3

The loss on drying of the tablets of Examples 2 and 3 after storage under opened conditions of 40° C. and 75% RH for 1 week was measured in a similar manner to that of Experimental Example 4. The results are shown in Table 6. The loss on drying in the tablets, which contained D-mannitol in the formulations, was low.

TABLE 6

|  | Loss on drying (%) |
|---|---|
| Example 2 | 1.3 |
| Example 3 | 1.4 |

From the above results, a stable formulation comprising Compound A or a pharmaceutically acceptable salt thereof can be provided by controlling the proportion of crystals of Compound A or a pharmaceutically acceptable salt thereof, and/or by using a pharmaceutical additive capable of controlling a water content in a formulation.

INDUSTRIAL APPLICABILITY

According to the present invention, a stable pharmaceutical composition for oral administration comprising Compound A or a pharmaceutically acceptable salt thereof, wherein the generation of related substances during storage, is inhibited.

Although the present invention has been described with reference to specific embodiments, various changes and modifications obvious to those skilled in the art are possible without departing from the scope of the appended claims.

The invention claimed is:

1. A pharmaceutical composition for oral administration comprising:
    6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate, wherein a proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate is 62% or more with respect to a total amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate in the pharmaceutical composition; and
    at least one pharmaceutical additive selected from the group consisting of lactose, D-mannitol, anhydrous dibasic calcium phosphate, calcium stearate, and talc.

2. The pharmaceutical composition according to claim 1, wherein a pharmaceutical additive content is 50% by weight to 90% by weight with respect to a total weight of the pharmaceutical composition.

3. The pharmaceutical composition according to claim 1, wherein the at least one pharmaceutical additive is D-mannitol.

4. The pharmaceutical composition according to claim 1, wherein the at least one pharmaceutical additive is lactose and/or D-mannitol.

5. The pharmaceutical composition according to claim 2, wherein the at least one pharmaceutical additive is D-mannitol.

6. The pharmaceutical composition according to claim 4, wherein a total content of lactose and/or D-mannitol is 50% by weight to 70% by weight with respect to a total weight of the pharmaceutical composition.

7. The pharmaceutical composition according to claim 3, wherein a total content of D-mannitol is 50% by weight to 70% by weight with respect to a total weight of the pharmaceutical composition.

8. The pharmaceutical composition according to any one of claims 1, 2-5, 6, and 7, which is a tablet.

9. A tablet comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate;
    at least one pharmaceutical additive selected from the group consisting of lactose, D-mannitol, anhydrous dibasic calcium phosphate, calcium stearate, an talc,
    wherein a total pharmaceutical additive content is from 50% to 90% by weight with respect to a total weight of the tablet, and
    wherein a proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate is 62% or more with respect to a total amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate in the tablet.

10. The tablet according to claim 9, wherein the pharmaceutical additive is lactose and/or D-mannitol.

11. The tablet according to claim 9, wherein the pharmaceutical additive is D-mannitol.

\* \* \* \* \*

UNITED STATES PATENT AND TRADEMARK OFFICE
CERTIFICATE OF CORRECTION

PATENT NO. : 10,786,500 B2
APPLICATION NO. : 15/741377
DATED : September 29, 2020
INVENTOR(S) : Masakazu Miyazaki et al.

It is certified that error appears in the above-identified patent and that said Letters Patent is hereby corrected as shown below:

On the Title Page

[56] REFERENCES CITED:
"385-388 (2006). S. Edge et al., "Lactose, Monohydrate," in Hand-" should read
--385-388 (2006). ¶S. Edge et al., "Lactose, Monohydrate," in Hand- --.

In the Specification

Column 2:
Line 32, "a incompatibility" should read --an incompatibility--.

Column 11:

TABLE 1

|  | Comparative Example 1 | Example 1 |
|---|---|---|
| Compound A hemifumarate | 11.05 | 44.2 |
| Lactose hydrate | 53.75 | 215.0 |
| Microcrystalline cellulose | 4.5 | 18.0 |
| Low-substituted hydroxypropyl cellulose | 9.0 | 36.0 |
| Hydroxypropyl cellulose | 1.8 | 7.2 |
| Microcrystalline cellulose | 4.5 | 18.0 |
| Low-substituted hydroxypropy cellulose | 4.5 | 18.0 |
| Magnesium stearate | 0.9 | 3.6 |
| Subtotal | 90.0 | 360.0 |
| Film-coating agent (Opadry 03F42203) | 2.7 | 10.8 |
| Total | 92.7 | 370.8 |

Lines 36-51 (Table 1), " Unit mg                                              " should read Signed and Sealed this
Fifth Day of January, 2021

Andrei Iancu
*Director of the United States Patent and Trademark Office*

TABLE 1

|  | Comparative Example 1 | Example 1 |
|---|---|---|
| Compound A hemifumarate | 11.05 | 44.2 |
| Lactose hydrate | 53.75 | 215.0 |
| Microcrystalline cellulose | 4.5 | 18.0 |
| Low-substituted hydroxypropyl cellulose | 9.0 | 36.0 |
| Hydroxypropyl cellulose | 1.8 | 7.2 |
| Microcrystalline cellulose | 4.5 | 18.0 |
| Low-substituted hydroxypropyl cellulose | 4.5 | 18.0 |
| Magnesium stearate | 0.9 | 3.6 |
| Subtotal | 90.0 | 360.0 |
| Film-coating agent (Opadry 03F42203) | 2.7 | 10.8 |
| Total | 92.7 | 370.8 |

-- Unit: mg --; and

TABLE 2

|  | Example 2 | Example 3 |
|---|---|---|
| Compound A hemifumarate | 44.2 | 44.2 |
| D-mannitol | 82.5 | 86.12 |
| Hydroxypropyl cellulose | 4.2 | 4.32 |
| Low-substituted hydroxypropyl cellulose | 7.0 | 7.2 |
| Magnesium stearate | 2.1 | 2.16 |
| Subtotal | 140.0 | 144.0 |
| Film-coating agent (Opadry 03F42203) | 4.2 | 4.3 |
| Total | 144.2 | 148.3 |

Lines 54-66 (Table 2), " Unit: mg " should

TABLE 2

|  | Example 2 | Example 3 |
|---|---|---|
| Compound A hemifumarate | 44.2 | 44.2 |
| D-mannitol | 82.5 | 86.12 |
| Hydroxypropyl cellulose | 4.2 | 4.32 |
| Low-substituted hydroxypropyl cellulose | 7.0 | 7.2 |
| Magnesium stearate | 2.1 | 2.16 |
| Subtotal | 140.0 | 144.0 |
| Film-coating agent (Opadry 03F42203) | 4.2 | 4.3 |
| Total | 144.2 | 148.3 | read -- Unit: mg --.

Column 15:
Line 17, "as similar" should read --similar--.

In the Claims

Column 18:
Line 56, "an talc," should read --and talc,--.